United States Patent
Kerschbaumer et al.

(10) Patent No.: US 6,499,998 B2
(45) Date of Patent: Dec. 31, 2002

(54) SHADE DETERMINATION APPARATUS AND METHOD FOR SPECIFYING AND DETERMINING COLORS FOR TEETH AND DENTAL RESTORATIONS

(75) Inventors: Harald Kerschbaumer, Klaus (AT); Armin Ospelt, Vaduz (LI)

(73) Assignee: Ivoclar Vivadent AG, Schaan (LI)

(*) Notice: Subject to any disclaimer, the term of this patent is extended or adjusted under 35 U.S.C. 154(b) by 31 days.

(21) Appl. No.: 09/821,567

(22) Filed: Mar. 29, 2001

(65) Prior Publication Data

US 2001/0049082 A1 Dec. 6, 2001

Related U.S. Application Data

(60) Provisional application No. 60/215,829, filed on Jul. 3, 2000.

(30) Foreign Application Priority Data

May 16, 2000 (DE) .......................... 100 23 840

(51) Int. Cl.[7] .............................................. A61C 19/10
(52) U.S. Cl. ..................................... 433/26; 433/203.1
(58) Field of Search ........................ 433/26, 29, 203.1, 433/215

(56) References Cited

U.S. PATENT DOCUMENTS

| | | | |
|---|---|---|---|
| 3,405,446 A | * 10/1968 | Wiener | 433/72 |
| 4,654,794 A | 3/1987 | O'Brien | 364/413 |
| 4,836,674 A | 6/1989 | Lequime et al. | 356/319 |
| 5,240,414 A | * 8/1993 | Thompson | 433/26 |
| 5,273,429 A | 12/1993 | Rekow et al. | 433/215 |
| 5,690,486 A | 11/1997 | Zigelbaum | 433/29 |
| 5,766,006 A | 6/1998 | Murijacic | |
| 5,800,164 A | 9/1998 | Pfau | 433/26 |
| 5,961,324 A | 10/1999 | Lehmann | 433/26 |
| 6,132,210 A | 10/2000 | Lehmann | 433/26 |
| 6,190,170 B1 | 2/2001 | Morris et al. | 433/215 |
| 6,206,691 B1 | 3/2001 | Lehmann et al. | 433/26 |
| 6,210,159 B1 | 4/2001 | Lehmann et al. | 433/26 |

FOREIGN PATENT DOCUMENTS

| | | |
|---|---|---|
| DE | 26 41 740 | 3/1978 |
| DE | 19611122 | 9/1997 |

* cited by examiner

Primary Examiner—Cary E. O'Connor
(74) Attorney, Agent, or Firm—Winston & Strawn

(57) ABSTRACT

In a shade determination apparatus for teeth and dental restorations, a set of reference templates for comparing to a patient's tooth is provided, whereby based on the coloration of the reference template the shade of a tooth or of a restoration to be employed can be determined. The reference templates are produced in a layer arrangement, taking into consideration layer thickness and/or material selection, that corresponds to the tooth or the dental restoration to be employed. A storage apparatus stores the coloration of the reference templates, and the layering of the tooth or of the dental restoration can be matched and determined based on partial images from an image of the patient's tooth.

27 Claims, 2 Drawing Sheets

SHADE DETERMINATION APPARATUS AND METHOD FOR SPECIFYING AND DETERMINING COLORS FOR TEETH AND DENTAL RESTORATIONS

This application claims benefit of Provisional Application Ser. No. 60/215,829 filed Jul. 3, 2000.

BACKGROUND OF THE INVENTION

The present invention relates to a shade or color determination apparatus for teeth and dental restorations, and also relates to a method for specifying and determining shades for teeth and dental restorations.

Such a shade determination apparatus and such a method are known from U.S. Pat. No. 5,766,006. This solution represents an advance relative to the use of a conventional shade guide. A commercial shade guide has a plurality of color groups, whereby in each group are located teeth with different color saturation and brightness and each group is assigned to a certain shade. The tooth in a shade guide can have a structure of one to five layers.

Such a shade guide has limited selection options. This limitation is not due to a lack of options for producing different color mixtures, but rather to the fact that even experienced dentists are limited in their ability to determine a shade correctly. One reason for this is that the eye becomes fatigued after long periods of comparison. But it is also due to the fact that the eye must observe the natural tooth and the prosthetic tooth held next to it in the shade guide in an "integrated" manner in order to obtain the results of the comparison. As a rule, the tooth in the shade guide has a two-layer structure and an overall thickness of 5 mm, whereby in the incisal region enamel material is applied thicker and in the cervical region dentine material is applied thicker.

An additional problem in the assessability of the reference teeth in the shade guide is that the teeth in the shade guide regularly comprise ceramics fired at high temperatures. Although such ceramics are more cost effective in terms of manufacture, manufacturing costs are substantial since they have to be distributed to all of the dentists. However, today it is not unusual for other ceramics to be used that are fired at temperatures lower than, e.g., 1300°. The newest materials for dental restorations always have optical properties that are similar to teeth, e.g. opal effects or brightness values determined by precisely-defined crystal sizes, whereby the optical refraction index is adjusted. Shade guides used in the past are generally not well suited for comparing shades with these new materials. The materials d.SIGN and Empress 2 are also among the new materials that have enhanced brightness even with better translucence. The shade guides that were used in the past are generally not well suited for comparing shades with these new materials.

In this regard, systems like that of the aforesaid US patent are not helpful because they use the known shade guides as the reference. However, since these are not accurate despite the tooth-like structure of their coloration, especially for particularly translucent teeth, such computer-supported systems only result in minor improvements despite the expense they involve.

Another problem that in the past could only be addressed unsatisfactorily, if at all, is the progression of both the color and the translucence from the cervical to the incisal region. The cervical region generally has a coloration that tends toward reddish and is a bit transparent. The prior art provides no or only minimal accommodations for this graduation.

OBJECTS AND SUMMARY OF THE INVENTION

The object of the invention is therefore to provide a shade determination apparatus and a corresponding method that are able to provide a tooth or a dental restoration in an aesthetically pleasing manner, whereby the shade comparison is made substantially easier for the dentist and in particular the coloration and translucence obtained matches adjacent teeth or adjacent regions.

This object is achieved in accordance with the apparatus and method of the present invention. In particular, the shade determination apparatus has a set of reference templates for comparison to a patient's tooth, whereby based on the coloration of the reference template the shade of a tooth or a restoration that is to be employed can be determined. The reference templates are produced in a layer arrangement, taking into consideration layer thickness and/or material selection, that corresponds to the tooth, dental restoration, or filling that is to be employed. The apparatus also has a storage apparatus in which the coloration of the reference template is stored and the layering of the tooth or dental restoration can be matched and determined based on partial images from an image of the patient's tooth. In the method, a set of reference templates is compared to a patient's tooth and based on the coloration of the reference template, the shade of a tooth or restoration that is to be employed can be determined. The reference templates are produced in a layer arrangement taking into consideration layer thickness and/or material selection that corresponds to the tooth or dental restoration that is to be employed. The coloration of the reference template is stored and the layering of the tooth or dental restoration can be matched and determined based on partial images from an image of the patient's tooth.

Surprisingly, the inventive measures make it possible for the first time to obtain adequate coloration, even in terms of perception of the human eye, for the tooth to be replaced or for dental restorations. This is based in particular or the fact that the reference templates are provided with layer thicknesses that correspond to the actual layer thicknesses of the incisal material and dentin material to be applied. Surprisingly this measure makes it possible to obtain a more natural appearance, even when the reference template is not in the shape of a tooth, because by recording the image with the same camera, the same assessment flows into the process for analyzing the natural tooth and the reference template. It is obvious that in this context it is important to reference the shades if the same camera is not used but an identical model camera is used. In order to prevent metamerism effects it is advantageous to provide identical lighting.

In accordance with the invention, it is advantageous to select the layer thicknesses to correspond to the layer thicknesses that occur in practice. For instance, a set of reference templates can be produced with layer thicknesses: incisal material 0.2 mm, dentine 1 mm, and opaque layer 0.1 mm. An additional set of reference templates can be produced with the layer thicknesses: incisal material 0.2 mm, dentine material 0.3 mm, and opaque layer 0.1 mm. An additional set can be produced with the layer thicknesses: incisal material 0.15 mm, dentine 0.4 mm, deep dentine 0.3 mm, and opaque layer 0.1 mm.

In accordance with the invention, it is particularly advantageous in this context that the different colorations can be matched by means of automatic comparison. It is preferable in this context for the recorded natural tooth to be displayed on the screen and sections of this tooth to be marked in a suitable manner, and then to find the correct reference template immediately, selecting the reference template as appropriate. In accordance with the invention it is particularly advantageous for the reference templates to have been fired from original materials in the original layer thickness, cost-related issues not having a negative impact thereupon. On the contrary, it is no longer necessary to divide up shade guides oneself; rather, reference templates can simply be produced with laboratory quality, the appropriate detectable parameters for the reference template then being recorded with a reference camera and stored in a data base. Even if procurement of the recording apparatus and the necessary software represents a certain monetary outlay, modified shades obtained in new materials or other types of shades can then be made available to the dentist or dental technician with no other measures required.

The accuracy of the comparison can be performed in accordance with the invention depending on the number of reference templates available in the data base such that differences are no longer visible. In accordance with the invention, it is advantageous when the regions of the tooth to be analyzed are pre-specified as the regions that are generally particularly critical. When the dentist wants to deviate from the standards, this can be done with no further action required by selecting other surfaces, whereby it is understood that the dentist also pre-specifies the type of material he wants, e.g. plastic or ceramic, and also pre-specifies whether or not an opaque layer will be used for facing metal frameworks.

In accordance with the invention it is particularly advantageous that the shade determination apparatus determines the layers in terms of material selection, layer thickness, and combination of materials for every section of the tooth or tooth restoration that is to be blended in with the analyzed natural tooth. Thus the dental laboratory obtains precise information about how the restoration should be performed. It is also possible to pre-select the complexity of each different stage. For instance, a switch can be provided for "complex" and "simple", which switch then pre-specifies more complex or simpler layers, as desired.

An additional parameter that must be determined for the dentist's or dental technician's comparison to the reference template is the layer thickness that will be available to him for a restoration. In this case as well there is an automatic comparison with the best option, since the reference templates are available in different overall layer thicknesses so that the different shades can be taken into account and included automatically in the assessment.

BRIEF DESCRIPTION OF THE DRAWINGS

Additional advantages, details, and features result from the following description of exemplary embodiments with the aid of the accompanying schematic drawings, in which.

DETAILED DESCRIPTION

Figure 1:
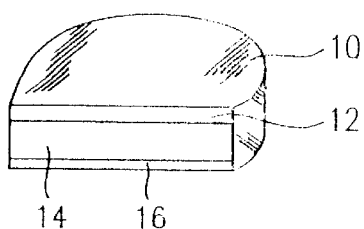
FIG. 1 is a perspective side elevation of a first reference template.

FIG. 1 illustrates a reference template as an example of a plurality of similar reference templates with the same layer thickness, with different colorations in the individual layers. The reference template 10 is formed as a circular tablet in the exemplary embodiment illustrated, but any other desired shapes can also be used. It has an overall thickness of 0.8 mm. The reference template comprises three layers, i.e., an enamel material layer 12 of 0.2 mm, a dentine material layer 14 of 0.5 mm, and an opaque layer 16 of 0.1 mm.

Such reference templates are now manufactured in a plurality of combinations in this layer thickness and recorded by means of a digital camera. The diameter of a reference template disk 10 is, e.g., 10 mm, that is, it is generally larger than a tooth in a labial or buccal view. For instance, 24 reference templates can be produced in this layer structure that have different colorations for the three provided layers, i.e., enamel material 12, dental material 14, and opaque layer 16. The reference templates are produced from originals, e.g. from applicant's d.SIGN dental ceramics shade standards so that they correspond to the actual layers in the tooth.

Figure 2:
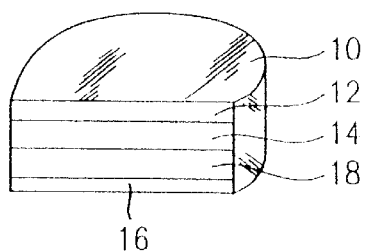
FIG. 2 is a perspective view of a second reference template.
Figure 3:
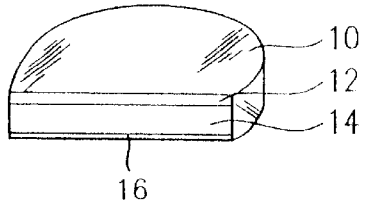
FIG. 3 is a perspective view of a third reference template.

FIG. 2 illustrates a modified structure of a reference template. The overall layer thickness of the reference template 10 in accordance with FIG. 2 is 1.3 mm. To facilitate illustration, the layer thicknesses in FIGS. 1 through 3 are exaggerated relative to the diameter of the reference template. The enamel material 12 has a thickness of 0.3 mm. Adjacent thereto is a dentine material layer 14 in which the layer thickness is 0.4 mm. Adjacent thereto is a layer made of a deep dentine material 18 that also has a thickness of 0.4 mm. The bottom-most layer is again an opaque layer 16 with a thickness of 0.2 mm.

It is obvious that in order to facilitate handling, the reference templates can be applied to any desired base ceramic. Since the opaque layer already completely faces at a thickness of 0.1 mm, the base layer for assessing the reference template is unimportant in terms of optics.

While the illustrated reference templates concern facing or veneered ceramics that are provided for restorations on a metal framework, it is obvious that in a corresponding manner reference templates made of ceramics for non-metal restorations can also be produced. For instance, applicant's Empress 2 ceramic product series can be used. The same applies to applicant's plastics, such as Targis and Vectris restoration materials.

While the reference template 10 from FIG. 1 is constructed with three layers, the reference template 10 in FIG. 2 has four layers. The reference template 10 in FIG. 2 can consequently be considered more complex and the reference template 10 in FIG. 1 can be considered more simple. Of course, instead of using the deep-dentine material 18 for the reference template in FIG. 2, it is also possible to use clear material, which results in a more translucent effect.

Another reference template 10 can be seen in FIG. 3; it has a minimum overall layer thickness of only 0.66 mm. Provided in this case is a combination of 0.12 mm enamel material 12, 0.4 mm dentine material 14, and 0.08 mm opaque layer 16.

It is obvious that as suitable materials are developed in the future that are appropriate for even thinner layer thicknesses, these can also be prepared and analyzed as reference templates in accordance with the invention.

Figure 4:
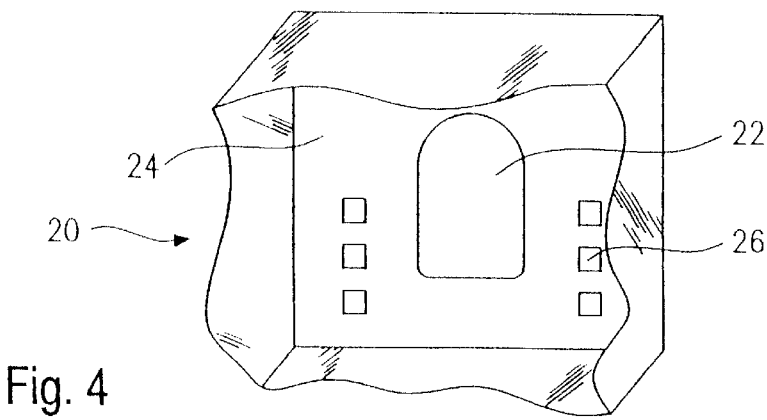
FIG. 4 is a perspective view of a receiving sheath.
Figure 7:
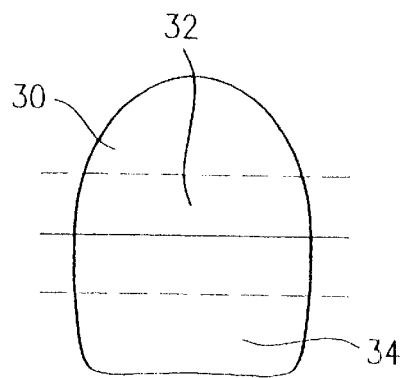
FIG. 7 illustrates two alternatives for horizontal partitioning.
Figure 8:
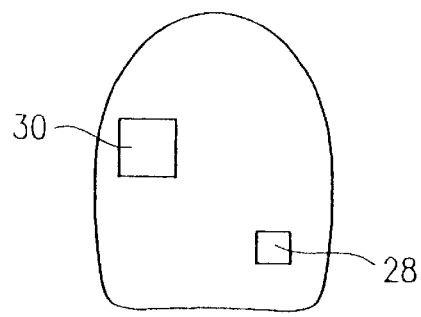
FIG. 8 illustrates variable fields for field partitioning.
Figure 9:
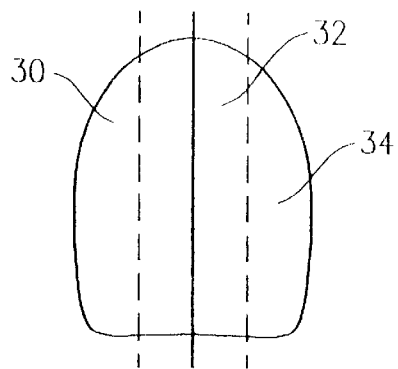
FIG. 9 illustrates vertical fields for field partitioning.

The reference templates are preferably analyzed in the same manner that the patient's teeth are later analyzed. Provided for this is a covering sheath 20, illustrated in FIG. 4, that is black in color on the inside and that has a recess 22 that substantially corresponds to the labial or buccal view of a tooth. The recess 22 is embodied in an end 24 of the sheath that is black on the inside, while the digital camera (not shown) is attached to the opposing end.

Such a covering sheath (20) not only fulfills the function of blocking out ambient light, it also ensures the correct distance between tooth and optics. In addition, it houses one or more shade reference templates that can be arranged, e.g., adjacent to the incisal edge.

In an alternative embodiment, provided instead of a cover in the shape of a tooth is some other type of cover, and in a further embodiment the shade reference template is positioned by means of an appropriate holder immediately below the incisal edge of the tooth.

Lateral to the recess 22, but clearly spaced therefrom, are provided a plurality of reference shade fields 26 that can be used for individual shade comparisons. It is important that these reference shades are extremely color-stable so that consideration should also be given to manufacturing them from ceramic materials.

For recording the reference template, the reference template is now placed on the other side of the recess 22. It is larger than the recess 22 so that it covers the recess 22 completely. A source of light is provided in the illustrated exemplary embodiment on the nearer side of the recess 22. It can either be integrated into the cover sheath 20 or connected from outside, whereby the light then strikes the end 24 preferably via a mirror. The light intensity is regulated, e.g. by the digital camera so that identical lighting is always maintained.

The reference templates, e.g. a total of 1000 templates for the different materials in numerous different combinations of layer thicknesses and colorations, are now recorded successively and the values obtained for the various possible recorded parameters are stored in a data base and assigned to the reference template.

Figure 5:
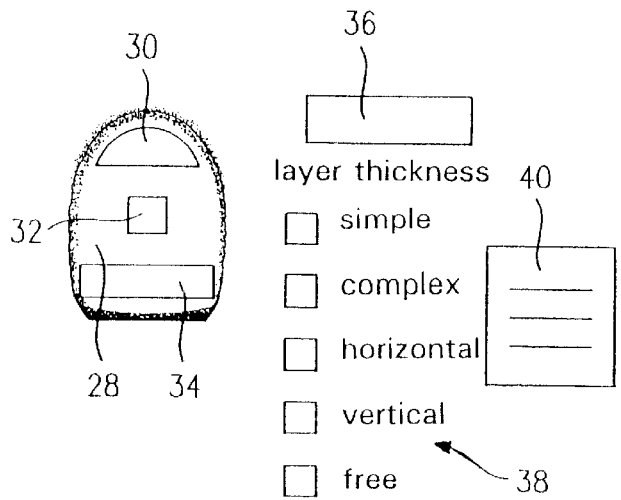
FIG. 5 illustrates a view of a screen of a color analyzing apparatus in accordance with the invention.

The data are made available to the dental laboratory or dental practice, together with an appropriate program and the digital camera and the covering sheath. Computers that are generally available anyway can be used. The dentist now records the patient's tooth. FIG. 5 illustrates an example of such a recording. Depending on the type of tooth and the restoration to be produced, the technician or dentist now decides whether a simple or complex layering should be used and what layer thickness is available. The type of field partitions or partial images can also be selected.

Figure 6:
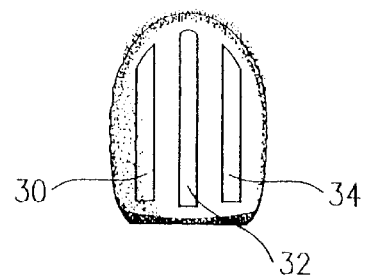
FIG. 6 illustrates another field partition in accordance with FIG. 5.

FIG. 5 illustrates horizontal partitioning of a patient's tooth 28. The patient's tooth 28 is to be recorded in horizontal partial images as specified by the dentist. Provided for this is a cervical partial image 30 that is overlaid over the tooth, a central partial image 32, and an incisal partial image 34. In addition, in a central area of the screen in a field 36 the dentist indicates the layer thickness that is available to the dental technician. In addition, provided below the field 36 in the illustrated exemplary embodiment are various switch boxes 38 that make it possible to specify the layering as simple or complex, and that furthermore make it possible to indicate whether horizontal partitioning or vertical partitioning of partial images is desired, or whether freely produced partial images is desired. A view with vertical partial images is illustrated in FIG. 6.

When the partial images are freely selected, the dentist can indicate fields across the tooth using a suitable indicating instrument. A mean is calculated for each partial image and compared to the data base. The result can be seen in the results field 40 so that the material selection is specified in detail for the dental technician in terms of shade, layer thickness, layer sequence, etc.

It is obvious that the type of material, i.e., metal ceramic, non-metal ceramic, or plastic, is either pre-specified from the very beginning or can be specified via additional input fields.

As can be seen from FIG. 5, the partial images 30, 32, and 34 can also be provided as vertical partial images. In this case the tooth in its entirety is integrated and the layer thickness is optimized according to a pre-specified template such that the incisal region has a larger dental enamel material portion and the cervical region has a larger dentine material portion.

It is obvious that numerous modifications and further developments of the shade determination apparatus in accordance with the invention are possible without deviating from the field of the invention. For instance, the reference templates 10 can also be produced such that they are arched in order to also be able to record the edge effects of the teeth when recording via the covering sheath 20. Another option is to integrate an incisal edge library. In this case, the dentist is provided suggested incisal edges that match the recording of the patient's tooth and that have been produced in a suitable manner and have been stored or even can be obtained from patient data. The tooth or tooth restoration to be produced can also be overlaid with the patient's tooth in order to make a virtual restoration possible and thus to make possible enhanced assessment.

In accordance with a further advantageous embodiment, the shade determination apparatus is also permitted to perform the production of the teeth with CIM technology.

In a further embodiment of the shade determination apparatus in accordance with the invention it is provided to use a virtual paintbrush in a manner similar to existing image processing programs and to thus construct the tooth virtually. For this, a suitable material, e.g. opaque material, dentine material, incisal material, is selected, the desired layer thickness is specified, and the region in which the material is to be built up is specified. The shade obtained can be seen immediately on the screen. In this manner construction can proceed layer by layer, whereby the resultant coloration and transparency effects are immediately visible. Since the natural sample (the recorded tooth) is in the immediate vicinity, the shade matching can be performed both visually and by comparing color parameters. Using this technique individual materials can also be exchanged and replaced with suitable materials until the desired effect has been achieved, whereby this technique can be used for crowns, bridges, and direct and indirect fillings.

Figure 10:
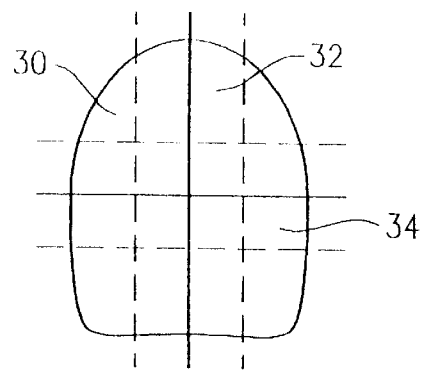
FIG. 10 illustrates field partitioning with combined vertical and horizontal partitioning.

FIGS. 7 through 10 illustrate different views of various field partition options, whereby in accordance with FIG. 10 horizontal and vertical partitions are combined.

While a preferred form of this invention has been described above and shown in the accompanying drawings, it should be understood that applicant does not intend to be limited to the particular details described above and illustrated in the accompanying drawings, but intends to be limited only to the scope of the invention as defined by the following claims.

What is claimed is:

1. A shade determination apparatus for teeth and dental restorations, comprising:

a set of reference templates for comparison to a patient's tooth, wherein based on the coloration of a reference template the shade of a tooth or a restoration that is to be employed can be determined, and wherein said reference templates are produced in a layer arrangement, taking into consideration at least one of layer thickness and material selection, that corresponds to a tooth, dental restoration or filling that is to be employed; and a storage device in which a coloration of said reference templates is stored and the layering of the tooth or dental restoration can be matched and determined based on partial images from an image of the patient's tooth.

2. A shade determination apparatus in accordance with claim 1, wherein said reference template has a layer thickness of 0.3 to 3 mm for the overall layer thickness of dentine material and enamel material and any opaque layer.

3. A shade determination apparatus in accordance with claim 1, wherein said reference templates have a single layer.

4. A shade determination apparatus in accordance with claim 1, wherein said reference templates are produced such that dentine material, incisal material, and opaque material are applied to dental alloys.

5. A shade determination apparatus in accordance with claim 1, wherein said reference templates have framework materials made of high-value glass ceramics or fiber-reinforced plastics.

6. A shade determination apparatus in accordance with claim 1, wherein said reference templates are stored in a data base and a matching reference template is addressed via a controlled region in the reproduced patient's tooth.

7. A shade determination apparatus in accordance with claim 1, wherein said reference templates are recorded under the same metamerical conditions as the patient's tooth.

8. A shade determination apparatus in accordance with claim 1, wherein said reference templates are recorded with a camera that is identical to that used to record the patient's teeth, at least in terms of optic and electrical properties.

9. A shade determination apparatus in accordance with claim 8, wherein said reference templates are recorded with the same camera that is used to record the patient's teeth.

10. A shade determination apparatus in accordance with claim 1, wherein the patient's tooth is reproduced on a screen and the next associated reference template can be indicated by marking a region of the representation of said patient'tooth.

11. A shade determination apparatus in accordance with claim 10, wherein said shade determination apparatus integrates via the marked region of the tooth on the screen and compares the figure so obtained to said reference template.

12. A shade determination apparatus in accordance with claim 11, wherein the marked region extends over the entire tooth or over a plurality of vertical and/or horizontal partitions.

13. A shade determination apparatus in accordance with claim 11, wherein the marked region extends in any desired number and any desired size of freely-selectable fields.

14. A shade determination apparatus in accordance with claim 13, wherein a value obtained is determined with respect to analyzable parameters such as shade, brightness, and saturation, and a reference template is selected via the comparison apparatus, wherein the sum of the deviations of the individual parameters is the lowest.

15. A shade determination apparatus in accordance with claim 1, wherein an image acquisition device is used to record an image of the patient's tooth, with the image essentially corresponding to the analyzed tooth.

16. A shade determination apparatus in accordance with claim 15, wherein the analyzed segment is determined by a covering, in particular a black covering, that has a through-recess in the shape of a tooth.

17. A shade determination apparatus in accordance with claim 16, wherein said covering also determines an imaging distance between the tooth and the image acquisition device.

18. A shade determination apparatus in accordance with claim 15, wherein, when the patient's tooth is recorded, provided to said patient's tooth adjacent to or below the incisal line edge are reference fields via which a recording apparatus can be calibrated for recording an image of the patient's tooth.

19. A shade determination apparatus in accordance with claim 15, wherein the image acquisition device is a digital camera or a video camera.

20. A shade determination apparatus in accordance with claim 15, wherein said recording apparatus is a digital camera.

21. A shade determination apparatus in accordance with claim 1, wherein said shade determination apparatus controls a CIM apparatus via which the layering of the artificial tooth or dental restoration to be manufactured can be determined in terms of material selection and layer thickness and the tooth can at least be pre-fabricated.

22. A shade determination apparatus in accordance with claim 1, wherein said reference templates are fired at the same temperature and with the same firing curve as the teeth or dental restorations.

23. A shade determination apparatus in accordance with claim 1, wherein said reference templates and the teeth or teeth restorations are made of light- and/or heat-curable plastics.

24. A shade determination apparatus in accordance with claim 1, wherein prior to producing the tooth or the tooth restoration, the provision of said selected reference template can be overlaid in the tooth shape on a screen and thus a virtual tooth restoration can be examined in a composite view with an adjacent tooth.

25. A shade determination apparatus in accordance with claim 1, wherein said storage apparatus has an incisal edge library that has incisal edges structured as they occur in nature and produced from the original materials in accordance with a layer structure communicated for dental technology, which edges can be overlaid on a screen in order to assess the results of the dental restoration when selecting the affected incisal edge library.

26. A shade determination apparatus in accordance with claim 1, wherein for producing the tooth or the dental restoration, a digital recording of the restoration can be overlaid on a screen and thus it is possible to compare said restoration to an adjacent tooth, whereby the comparison is either visual or is performed by analyzing and comparing shade, saturation, and brightness.

27. A shade determination apparatus in accordance with claim 1, wherein said reference template has a layer thickness of between 1 and 2 mm for the overall layer thickness of dentine material and enamel material and any opaque layer.

* * * * *